United States Patent [19]

Crosby et al.

[11] Patent Number: 5,321,268

[45] Date of Patent: Jun. 14, 1994

[54] UNDERSEA PROBE

[75] Inventors: David A. Crosby; Philip A. Ekstrom, both of Shaw Island, Wash.

[73] Assignee: Northwest Marine Technology, Inc., Shaw Island, Wash.

[21] Appl. No.: 20,814

[22] Filed: Feb. 22, 1993

[51] Int. Cl.$^5$ ............................................... G01J 1/58
[52] U.S. Cl. ................................. 250/361 R; 250/367; 250/368
[58] Field of Search ............ 250/361 R, 458.1, 483.1, 250/486.1, 372, 368, 367

[56] References Cited

U.S. PATENT DOCUMENTS

| | | | |
|---|---|---|---|
| 4,350,890 | 9/1982 | Geelhood et al. | 250/372 |
| 4,371,897 | 2/1983 | Kramer | 250/458.1 X |
| 4,467,208 | 8/1984 | Müller et al. | 250/483.1 |
| 4,788,436 | 11/1988 | Koechner | 250/361 R X |
| 4,790,090 | 12/1988 | Sharber | 40/300 |

*Primary Examiner*—Constantine Hannaher
*Assistant Examiner*—Edward J. Glick
*Attorney, Agent, or Firm*—Kenyon & Kenyon

[57] ABSTRACT

An undersea probe which can be attached to marine animals for collecting data as to light intensity and temperature in regions where the marine animals travel. The probe is essentially omnidirectional in its light acceptance capability so that light intensity measurements will not be dependent upon any particular orientation of the probe. The probe includes a central optical fiber containing a fluorescent dye enclosed in a transparent or translucent, protective and fouling-resistant sheath. The optical fiber is provided at its outer end with a fiber terminator which blocks entry of light into the end of the fiber. At its opposite inner end, the fiber is coupled to a light detector in a housing which may be implanted in the marine animal. The optical fiber exhibits radial changes in its refractive index to trap light which approaches the surface of the fiber from inside and which makes a small enough angle with that surface. Such light is propagated along the fiber to the light detector.

24 Claims, 1 Drawing Sheet

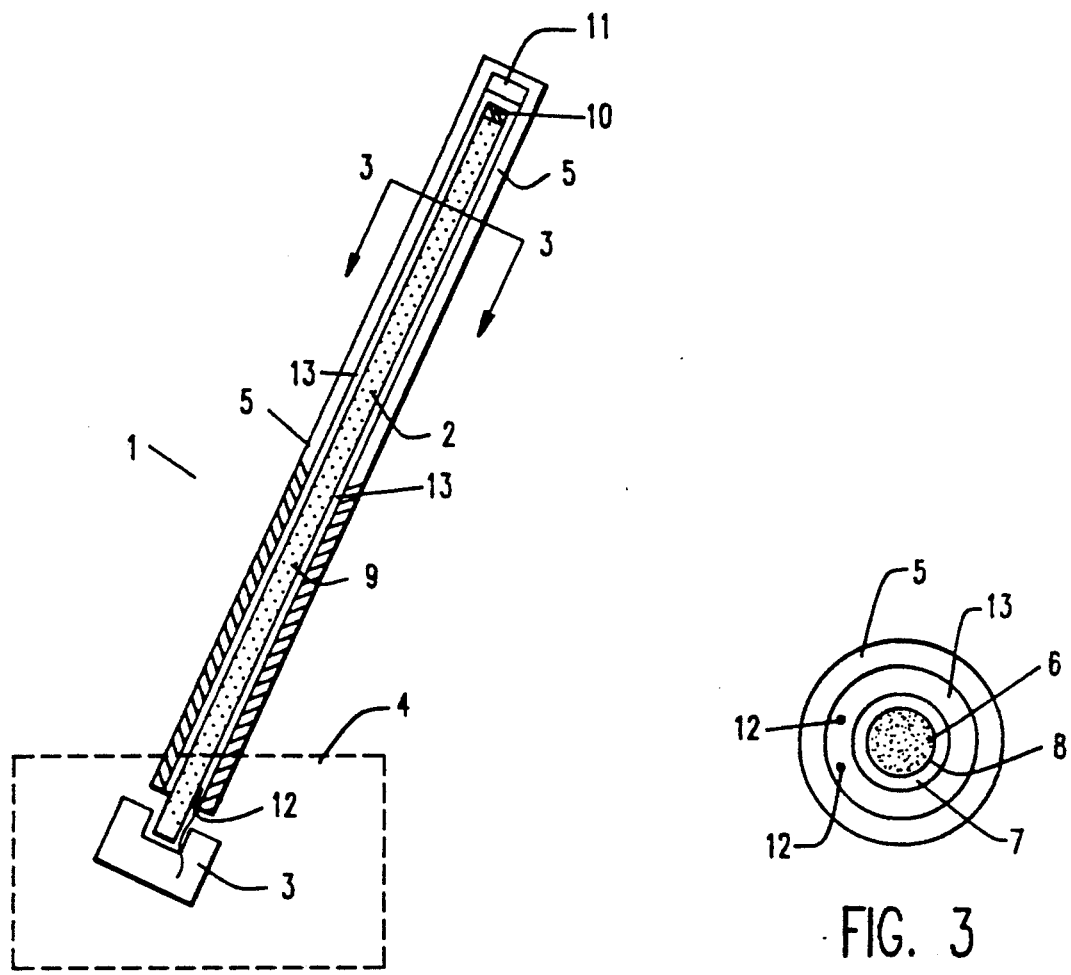

UNDERSEA PROBE

BACKGROUND OF THE INVENTION

1. Field of the Invention

The invention relates to a probe for attachment to land and marine animals which is capable of detecting and measuring light, and more particularly to such a probe which is wavelength-selective and which detects light from essentially all directions so that the measurements are not dependent upon any particular orientation of the probe.

2. Description of Related Art

Attempts have been made to determine and study the migration and/or wandering patterns of certain forms of marine life, particularly species of fish which have been threatened with extinction due to, for example, intense fishing pressure. For example, due to their high value in the far east marketplace, blue fin tuna have been particularly victimized in recent years to the point where the population of this tuna has dropped by a factor of about ten.

One way which has been used to learn some information about the movements of fish is by tagging the fish with markers such as color-coded visible implant tags. Such tags allow for the identification of fish, so that upon recapture of a particular fish, it can be learned to what location that fish travelled.

Although the tagging method provides information as to the ultimate location of a particular fish upon recapture, this method does not yield any information as to the route by which the fish moved from a point A to a point B. It would be desirable to learn more information as to the route which the fish took in its journey for the purpose of determining, for example, whether the particular fish migrates or merely wanders.

In an attempt to learn more information about the journey of a fish from one location to another, photo detecting devices and thermistors have been developed for attachment to the fish. Upon recapture of the fish, the light intensity information measured by the photo detector and recorded along with time-of-day information by some means in the device can be interpreted to learn the geographic longitude of the fish each day by noting the time of sunrise and sunset and performing standard calculations of celestial navigation. Temperature measurements taken by the thermistor and also recorded can be compared to known reference values of ocean temperature to yield information about the latitude of the fish during its travels.

One major problem encountered with the use of such photo detecting devices is that the measurement of the ambient light intensity may depend on the orientation of the detector because it is not held in a fixed orientation with respect to both the water surface and the direction of the sun. This can result in data which is not useful because it will not accurately reflect the true location of the fish. Therefore, it would be desirable for the photo detector to have a very broad light acceptance angle, or, ideally, that it be omnidirectional so that the measurement of ambient light intensity does not depend on the instrument's orientation.

Another problem encountered is that when the light measurement is made at some depth in the ocean some light is absorbed by the intervening water. The values measured must be corrected to take into account this absorption.

Yet another problem encountered with the use of light detecting devices is that ocean water is a conductive fluid which readily promotes corrosion of exposed metallic surfaces. In addition, sea water is known to promote the fouling of exposed photo detector surfaces.

Photo detectors with an optical filter which passes only a narrow range of wavelengths and with a diffuser which broadens its acceptance angle are known. In addition, it is known to arrange multiple sensors in a single probe so that only nonmetallic and fouling-resistant surfaces are exposed to the sea water. However, heretofore, it has not been possible to combine these known structures in the form of a thin, flexible probe which can extend through the skin of the fish into the surrounding sea water. In particular, a major problem in creating such a device is the fact that an effective diffuser is ordinarily large compared to the detector surface itself. Therefore, it would be an improvement in the art to integrate all of the above-referenced functions in a thin, flexible structure.

SUMMARY OF THE INVENTION

It is an object of the invention to provide a probe for use in detecting and measuring light intensity underseas whose measurements are not dependent on the particular orientation of the probe with respect to the water surface and the direction of the sun.

It is a further object of the invention to provide such a probe having a very broad light acceptance angle such that it is essentially omnidirectional.

It is a further object of the invention to provide such a probe which is thin and flexible and which can be attached to a fish in such a way that it extends through the skin of the fish into the surrounding sea water.

It is yet a further object of the invention to provide such a probe which measures light only within a selected band of wavelengths.

These and other objects are achieved by the present invention which provides a probe for attachment to a fish such as a Tuna. The probe includes a light detector system which is attached at the end of an elongated thin optical fiber. The photo detector is implanted beneath the skin of the fish leaving the elongated optical fiber outside to project into the water. The optical fiber is encased in a sheath of a translucent, protective, fouling-resistant coating. The end of the optical fiber which is opposite the photo detector system is capped with a fiber terminator which blocks entry of light into the fiber through that end. In this way, light may only enter the optical fiber transverse to the sides of the fiber (i.e., at an angle to the longitudinal direction of the fiber). Preferably, the fiber terminator belongs to a thermistor which is coupled to a microprocessor in the photo detector system housing.

The optical fiber includes a fluorescent dye which preferably has a relatively narrow excitation spectrum around a wavelength of 465 nm. The optical fiber is defined by an imaginary longitudinal axis, and the refractive index of the fiber changes in the radial direction away from the axis. Preferably, the core of the optical fiber has a refractive index which is slightly greater than the refractive index of the outermost region of the fiber.

When light having a wavelength within the excitation spectrum is incident on the side of the optical fiber, the dye absorbed in the fiber is excited and fluoresces to reemit light of a longer wavelength. As the light is reemitted, it is refracted due to the difference in the refractive index in the radial direction of the fiber.

However, a portion of the reemitted light which makes a small enough angle with the outer surface of the fiber is, when refracted, trapped inside the fiber, and the portion which is refracted in the direction of the photo detector will be transmitted along the optical fiber to the photo detector where it is measured and recorded in a semiconductor memory. Likewise, temperature measurements from the thermistor are also stored.

Upon recapturing the fish, the device is removed, and the light intensity data, temperature data and any other data which has been stored may be read out through windows in the housing using a data link. The data is interpreted in a known manner by employing standard navigation calculations and by comparing it to reference values, thereby providing information about the longitude and latitude of the fish during its journey.

BRIEF DESCRIPTION OF THE DRAWINGS

FIG. 1 is a perspective view of a portion of the back of a Tuna with a measurement-recording system of the probe of the invention implanted in its dorsal muscle, and the optical fiber section of the probe extending into the water above the fish through an otherwise closed incision originally made to implant the system.

FIG. 2 is a cross-sectional view of the probe of this invention.

FIG. 3 is a cross-sectional head on view of the probe of FIG. 2 taken along the line 3—3.

DETAILED DESCRIPTION OF THE INVENTION

Referring to FIGS. 1 and 2, the probe of the invention is generally designated at 1 and includes an elongated, slender optical fiber 2 coupled at one end to a photo or light detector 3 located in a measurement system housing 4. The photo detector for measuring the intensity of light received from the optical fiber 2 and the electrical components for recording and storing data from the photo detector are housed in housing 4 which, as illustrated in FIG. 1, is intended to be implanted inside the fish. The optical fiber 2 will project into the water where it will receive light to be transmitted to the photo detector in the manner to be described.

The optical fiber 2 is covered with a sheath of a translucent, protective and fouling-resistant coating 5 to protect it from the hostile ocean or sea environment. The coating material may be, for example, a fluorocarbon plastic such as polytetrafluoroethylene, which is sold under the trade name TEFLON TFE. Preferably, the probe may also include a layer of a translucent silicone gel 13 interposed between the outer surface of the optical fiber 2 and the protective coating 5. As will be described herein, the silicone gel layer 13 preferably contains the wires needed to establish electrical communication between electrical components in the housing 4 and sensors attached to the optical fiber 2.

Suitable optical fibers for use in the probe are commercially available. The commercially available optical fibers typically include a polystyrene core 6 (see FIG. 3) surrounded by an outer layer or "cladding" 7 of a clear acrylic polymer, such as a (meth)acrylate polymer. In this invention, it is required to use an optical fiber whose core (e.g., polystyrene) has absorbed therein a fluorescent dye to serve as a light diffuser. Optical fibers having fluorescent dyes absorbed therein are also available.

Fluorescent dyes all exhibit the property of wavelength conversion. They absorb light at one wavelength or band of wavelengths and reemit light of a different color, always at a longer wavelength. Commercially common colorants typically absorb light in the blue and ultraviolet, and reemit other colors of the visible spectrum. Optical fibers which include fluorescent dyes have become known as "wave-shifter fibers" because of their property of reemitting light having a longer wavelength.

In selecting a dye for use in the present invention, one should consider the fact that sea water absorbs light, and that the degree of attenuation of white light ordinarily increases in a complex way with increasing depth. This can make interpretation of the data very complicated. However, out of all the light in the visible spectrum, blue light having a wavelength band around 465 nm is absorbed the least by sea water, and the attenuation of blue light with depth exhibits a simple exponential, rather than a superposition of many exponentials. Therefore, in accordance with the present invention, it is preferred to use a dye which exhibits only a very narrow excitation spectrum for a specific wavelength band around 465 nm in order to facilitate interpretation of the light intensity data. The compound known as Alberta Yellow is an example of such a dye. However, the most preferred fluorescent dye which exhibits a narrow excitation spectrum around 465 nm is the dye designated as F-COT ™ available from the Bicron Corporation, Cleveland, Ohio. Other dyes preferred over Alberta Yellow include dyes having these spectral characteristics from the Rhodamine and Coumarin families of fluorescent dyes.

In the present invention, the optical fiber 2 functions as a diffuser, broadening the light acceptance angle of the probe. In addition, the fiber 2 functions as a wavelength filter for the incident light since only light in the excitation band (preferably around 465 nm) causes fluorescence.

The outer layer or cladding 7 of the fiber 2 has a smaller index of refraction than the core 6 of the fiber. The difference between the index of refraction of the core and the index of refraction of the cladding causes light which traverses the interface 8 between these layers to bend or refract. Thus, light reemitted from the fiber upon fluorescence will be refracted. Most of the reemitted light (i.e., about 96%) will escape from the fiber, notwithstanding the refraction thereof. However, a small percentage of the reemitted light (i.e., about 4%) from the core 6 of the fiber 2 will make a sufficiently small angle with the interface 8 between the core 6 and the cladding 7 so that upon refraction, the reemitted light will not be able to escape from the optical fiber. The reemitted light which cannot escape will be propagated along the optical fiber in the longitudinal direction. The portion of the light which is propagated in the direction of the housing 4 will be detected and measured by the photo detector.

Light originating outside the fiber and not having its direction changed by being absorbed by the dye and reemitted cannot make the required small angle with the core-cladding boundary 8, and will pass out of the fiber again instead of propagating down it. Therefore, only light which has been absorbed by the fluorescent dye and reemitted within the fiber can reach the photodetector.

The fluorescent dye will ordinarily have some weak absorption of its own emitted light, and that absorption sets a limit to the length of dyed fiber which will efficiently transmit light. Alberta Yellow mentioned above is an example of such a dye. The length of fiber which can be used before absorption becomes significant depends on several factors such as dye concentration, but is typically a meter or more. The absorption is not significant enough to pose any problem in the present invention. Typically, in the case of a fiber which is about 25 cm or less in length dyed with F-COT ™, the absorption effect is negligible. The preferred length of the fiber of the present invention is about 25 cm.

In order to define the sensitive region of the light detector, the probe preferably includes a transmitting region 9 of the optical fiber 2 which is prevented from responding to external light, but instead just transmits light originating in the portion of the optical fiber 2 which contains the fluorescent dye. The portion of the optical fiber containing the dye may be referred to as the wave-shift region. The transmitting region 9 of the optical fiber 2 is located between the system housing 4 and the wave-shift region. The transmitting region 9 may be distinguished by being shielded from external light. This can be accomplished by painting the outer surface of the transmitting region, or, the portion of the sheath or coating 5 around the transmitting region 9 could be opaque so that non-propagating light cannot be incident on the transmitting region 9 of the optical fiber. Alternatively, the transmitting region 9 may be distinguished by not containing dye. In the latter case, any self-absorption of reemitted light by dye is avoided in region 9. It will be appreciated that where the transmitting region 9 contains no dye, an opaque coating or painting is not necessary to block light incident thereon since such incident light will be transverse to the fiber and pass right through it without any chance of being propagated down the fiber. Thus, in both cases, the transmitting region 9 will function merely as a conduit between the wave-shift region and the photo detector. In this way, only the wave-shift region of the optical fiber will be able to absorb light which is incident on the probe, and the only light which will be transmitted to the photo detector will be light which is reemitted from the wave-shift region and refracted so as to propagate along the longitude of the fiber.

The free end of the wave-shift region of the optical fiber (i.e., the end which is opposite the transmitting region 9 and the housing 4) is attached to a terminal opaque blocker 10 which prevents light from entering through the end of the optical fiber directly in the longitudinal direction, and prevents any light incident from this direction from being propagated down the length of the optical fiber. Such light would be subject to neither the wavelength filtering nor the diffusing effects of the fluorescent dye. Therefore, the only light which may be propagated down the optical fiber to the photo detector is light which is incident on the dyed portion of the fiber in a transverse direction (i.e., in a radial direction) and which is reemitted and refracted so as to become trapped in the fiber and enter a propagating mode (i.e., the light will propagate along the length of the fiber). Only about 4% of all the light which is incident on the wave-shift region of the optical fiber will be trapped and propagated.

Since half of the light generated in the propagating mode in the wave-shift region of the fiber will travel in each direction, it is preferable to have the terminal blocker 10 be reflective on its side which faces and which is attached to the end of the optical fiber. In this way, that half of the reemitted light which originally propagated away from the light detector housing 4 will be reflected toward the housing 4.

Since no light may be allowed to enter the end of the fiber 2, the region at the end of the fiber may also be used for mounting some other sensor, such as a bead or flake thermistor 11 for the measurement of temperature. Lead wires 12, sufficiently small to avoid significant shadowing on the optical fiber 2 may be run along the length of the probe inside the silicone gel layer 13 between the outer coating 5 and the optical fiber 2. Since optical fibers are ordinarily thin and flexible and since the coating or sheath 5 can preserve some measure of that flexibility, the invention provides a thin, flexible sensor probe integrating wavelength selection, optical diffusion, and optionally also temperature measurement.

In another embodiment of the invention, the single optical fiber 2 may be replaced by a bundle of multiple fiber strands. This can offer an advantage in increasing flexibility, and can permit the lead wires 12 for the sensor (e.o., thermistor) to pass up the center of the bundle where they do not cause asymmetric shadowing of the fiber bundle and are partly protected from stretching as the bundle is flexed. A hollow fiber can provide the same advantages except it will lack any significant increase in flexibility.

The light detector 3 located in the measurement system housing 4 receives and measures the intensity of the reemitted propagating light from the optical fiber 2. The light detector 3 may be a conventional silicon diode with an analog-to-digital converter and a microprocessor having semiconductor memory for storing the light intensity measurements. When another sensor, such as a thermistor 11 for detecting water temperature is included in the probe, the measurement system housing 4 will include a multiplexer coupled to wires 12 and also to the photo detector and analog-to-digital converter which will allow the analog-to-digital converter, microprocessor and memory to also store the temperature data.

The probe of the invention can be attached to a marine animal, such as a Tuna, by making an incision in the back of the Tuna and implanting the measurement system housing in the dorsal muscle. The optical fiber section 2 of the probe will project outside the fish into the water. If desired, a separate identification tag may be applied to the fish before releasing it.

Upon recapture of the fish to which the probe of the invention has been attached, the system housing 4 may be easily removed and the stored light intensity measurements (and temperature measurements, if applicable) may be read out in a known manner. The data may be interpreted in a conventional and well known manner by comparing it to standard reference values which reflect longitude and latitude positions.

In the foregoing specification, the invention has been described with reference to specific exemplary embodiments thereof. It will, however, be evident that various modifications and changes may be made thereunto without departing from the broader spirit and scope of the invention as set forth in the appended claims. For example, although the utility of the probe discussed herein is in the tracking of ocean life, its use is not so limited. The probe will also find application with freshwater fish, such as sturgeon, as well as with land animals. The specification and drawings are accordingly to be regarded in an illustrative rather than a restrictive sense.

We claim:

1. A probe for detecting light comprising:
an elongated slender optical fiber having a core which has a fluorescent dye absorbed therein and having an outer region coaxially disposed around the core, the core being characterized by at least a first index of refraction, and the outer region being characterized by at last a second index of refraction, the second index of refraction being different from the first index of refraction such that the optical fiber is capable of refracting light emitted from the core upon fluorescence of the dye such that a portion of said light emitted upon fluorescence will be refracted in a longitudinal direction along said optical fiber and will be propagated along said optical fiber;
a means for receiving and detecting light propagated along the optical fiber which is coupled to a first end section of the optical fiber;
a means for blocking light incident in the longitudinal direction of the optical fiber on a second end of the optical fiber such that the optical fiber may only receive light in directions which are transverse to the longitudinal direction; and
a translucent and fouling-resistant sheath around the outer region of the optical fiber.

2. The probe according to claim 1 wherein the fluorescent dye is characterized by an excitation spectrum band which has a peak for a wavelength of about 465 nm.

3. The probe according to claim 2 wherein the second index of refraction is less than the first index of refraction.

4. The probe according to claim 1 wherein the means for receiving and detecting light includes a silicon diode.

5. The probe according to claim 1 further comprising a means for measuring water temperature.

6. The probe according to claim 5 wherein the means for measuring water temperature is a thermistor.

7. The probe according to claim 6 wherein the thermistor is a component of the means for blocking light.

8. The probe according to claim 6 further comprising a microprocessor, a housing enclosing the microprocessor and the means for detecting light, a lead wire coupling the means for measuring water temperature with the microprocessor, and a multiplicity f additional elongated slender optical fibers which have a first end section coupled to the means for receiving light and a second end which is blocked by the means for blocking light and wherein the lead wire runs between said optical fibers.

9. The probe according to claim 8 wherein the fluorescent dye is characterized by an excitation spectrum band which has a peak for a wavelength of about 465 nm.

10. The probe according to claim 5 wherein the fluorescent dye is characterized by an excitation spectrum band which has a peak for a wavelength of about 465 nm.

11. The probe according to claim 1 further comprising a transmitting optical fiber, which does not include a fluorescent dye, coupling the means for detecting light with the slender optical fiber for transmitting propagating light from the slender optical fiber to the means for detecting light.

12. The probe according to claim 11 wherein the slender optical fiber is continuous and integral with the transmitting optical fiber.

13. The probe according to claim 1 wherein the translucent sheath is a coating of a fluorocarbon plastic.

14. The probe according to claim 13 wherein the translucent sheath is a coating of polytetrafluoroethylene.

15. The probe according to claim 1 further comprising a reflector means, attached to the means for blocking light, for reflecting light propagating along the optical fiber toward the means for blocking in an opposite direction toward the means for detecting light.

16. The probe according to claim 1 further comprising a housing for enclosing the means for detecting light, wherein the optical fiber projects outwardly to the exterior of the housing.

17. The probe according to claim 1 wherein the second index of refraction is less than the first index of refraction.

18. A probe for detecting light comprising:
an elongated slender optical fiber having a core which has a fluorescent dye absorbed therein and having an outer region coaxially disposed around the core, the core being characterized by at least a first index of refraction, and the outer region being characterized by at least a second index of refraction, the second index of refraction being different from the first index of refraction such that the optical fiber is capable of refracting light emitted from the core upon fluorescence of the dye such that a portion of said light emitted upon fluorescence will be refracted in a longitudinal direction along said optical fiber and will be propagated along said optical fiber;
a light detector, coupled to a first end section of the optical fiber, for receiving light propagated along the optical fiber;
a housing around the light detector, wherein the optical fiber projects outwardly to the exterior of the housing; and
a means for blocking light incident in the longitudinal direction of the optical fiber on a second end of the optical fiber such that the optical fiber may only receive light in directions which are transverse to the longitudinal direction.

19. A probe for detecting light underseas comprising:
an elongated slender optical fiber having a core which has a fluorescent dye absorbed therein and having an outer region coaxially disposed around the core, the fluorescent dye being characterized by an excitation spectrum band which is specific for blue light such that the dye fluoresces essentially only upon absorption of blue light, the core being characterized by at least a first index of refraction, and the outer region being characterized by at least a second index of refraction, the second index of refraction being different from the first index of refraction such that the optical fiber is capable of refracting light emitted from the core upon fluorescence of the dye such that a portion of said light emitted upon fluorescence will be refracted in a longitudinal direction along said optical fiber and will be propagated along said optical fiber;
a light detector, coupled to a first end section of the optical fiber, for receiving light propagated along the optical fiber; and a means for blocking light incident in the longitudinal direction of the optical fiber on a second end of the optical fiber such that the optical fiber may only receive light in directions which are transverse to the longitudinal direction.

20. The probe according to claim 19 wherein the excitation spectrum band of the fluorescent dye has a peak for a wavelength of about 465 nm.

21. The probe according to claim 19 further comprising a means for measuring water temperature.

22. The probe according to claim 19 further comprising a reflector means, attached to the means for blocking light, for reflecting light propagating along the optical fiber toward the means for blocking in an opposite direction toward the light detector.

23. The probe according to claim 19 further comprising a housing for enclosing the light detector, wherein the optical fiber projects outwardly to the exterior of the housing.

24. The probe according to claim 19 wherein the second index of refraction is less than the first index of refraction.

* * * * *